United States Patent [19]

Oesterhelt et al.

[11] Patent Number: 4,652,089
[45] Date of Patent: Mar. 24, 1987

[54] LIQUID CRYSTALLINE COMPOUNDS AND MIXTURES

[75] Inventors: Gottfried Oesterhelt, Reinach; Martin Petrzilka, Kaiseraugst, both of Switzerland

[73] Assignee: Hoffmann-La Roche Inc., Nutley, N.J.

[21] Appl. No.: 663,652

[22] Filed: Oct. 22, 1984

[30] Foreign Application Priority Data

Nov. 2, 1983 [CH] Switzerland .................. 5912/83
Aug. 20, 1984 [CH] Switzerland .................. 3970/84

[51] Int. Cl.$^4$ .................. C07C 69/75; C07C 121/00; C09K 19/30; C09K 3/04; G02F 1/13
[52] U.S. Cl. .................. 350/350 R; 252/299.5; 252/299.63; 252/299.65; 350/350 S; 560/102; 560/116; 558/411; 558/416
[58] Field of Search .................. 252/299.63, 299.65, 252/299.5; 350/350 R, 350 S; 260/465 D, 465 C, 465 R; 560/102, 116, 1

[56] References Cited

U.S. PATENT DOCUMENTS

| | | | |
|---|---|---|---|
| 4,035,056 | 7/1977 | Coates et al. | 252/299.66 |
| 4,149,413 | 4/1979 | Gray et al. | 252/299.63 |
| 4,261,651 | 4/1981 | Gray et al. | 252/299.63 |
| 4,261,652 | 4/1981 | Gray et al. | 252/299.62 |
| 4,387,038 | 6/1983 | Fukui et al. | 252/299.63 |
| 4,387,039 | 6/1983 | Sugimori et al. | 252/299.63 |
| 4,393,258 | 7/1983 | Sato et al. | 252/299.63 |
| 4,400,293 | 8/1983 | Romer et al. | 252/299.63 |
| 4,439,015 | 3/1984 | Rich et al. | 252/299.63 |
| 4,472,592 | 9/1984 | Takatsu et al. | 252/299.63 |
| 4,477,369 | 10/1984 | Sugimori et al. | 252/299.63 |
| 4,487,954 | 12/1984 | Sugimori et al. | 252/299.63 |
| 4,502,974 | 3/1985 | Sugimori et al. | 252/299.63 |
| 4,526,704 | 7/1985 | Petrzilka et al. | 252/299.63 |
| 4,550,981 | 11/1985 | Petrzilka et al. | 252/299.65 |
| 4,584,120 | 4/1986 | Fujii et al. | 252/299.63 |

FOREIGN PATENT DOCUMENTS

| | | | |
|---|---|---|---|
| 44646 | 1/1982 | European Pat. Off. | 252/299.63 |
| 87102 | 8/1983 | European Pat. Off. | 252/299.63 |
| 87032 | 8/1983 | European Pat. Off. | 252/299.63 |
| 103681 | 3/1984 | European Pat. Off. | 252/299.63 |
| 129177 | 12/1984 | European Pat. Off. | 252/299.63 |
| 149208 | 7/1985 | European Pat. Off. | 252/299.63 |
| 3237367 | 4/1983 | Fed. Rep. of Germany | 252/299.63 |
| 3211601 | 10/1983 | Fed. Rep. of Germany | 252/299.63 |
| 3224774 | 1/1984 | Fed. Rep. of Germany | 252/299.63 |
| 3317597 | 11/1984 | Fed. Rep. of Germany | 252/299.63 |
| 57-9742 | 1/1982 | Japan | 252/299.63 |
| 57-159743 | 10/1982 | Japan | 252/299.63 |
| 57-209252 | 12/1982 | Japan | 252/299.63 |
| 58-8023 | 1/1983 | Japan | 252/299.63 |
| 58-8022 | 1/1983 | Japan | 252/299.63 |
| 58-136680 | 8/1983 | Japan | 252/299.63 |
| 2086385 | 5/1982 | United Kingdom | 252/299.63 |
| 2092169 | 8/1982 | United Kingdom | 252/299.63 |
| 2107773 | 5/1983 | United Kingdom | 252/299.63 |

OTHER PUBLICATIONS

Gray, G. W., Mol. Cryst. Liq. Cryst., vol. 63, pp. 3–18, (1981).
Chem. Abst., 100:2797F, (Aug. 13, 1983).
Chem. Abst., 100:1655204, (May 14, 1984).

*Primary Examiner*—Teddy S. Gron
*Attorney, Agent, or Firm*—Jon S. Saxe; Bernard S. Leon; Mark E. Waddell

[57] ABSTRACT

This invention concerns compounds of the formula:

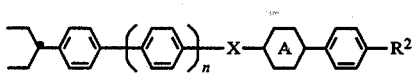

wherein
n is 1 and X is —COO—, —OOC— or —CH$_2$CH$_2$—; or
n is 0 and X is —CH$_2$CH$_2$—;
ring A is p-phenylene or trans-1,4-cyclohexylene;
$R^2$ is cyano, p-cyanophenyl or, when X is —COO— or —OOC—, $R^2$ may also be p-$R^3$-phenyl or trans-4-$R^3$-cyclohexyl;
and $R^1$ and $R^3$ each are straight-chain $C_1$-$C_{10}$-alkyl.

their manufacture and their use for electro-optical purposes and in gas chromatography are described.

9 Claims, 1 Drawing Figure

RETENTION TIME

SEPARATION OF AROMATIC HYDROCARBONS
(IN ACCORDANCE WITH EXAMPLE 9)

LIQUID CRYSTALLINE COMPOUNDS AND MIXTURES

BACKGROUND OF THE INVENTION

1. Field of the Invention

The present invention concerns liquid crystal compounds and mixtures as well as electro-optical devices containing same. The invention also concerns method of manufacturing these liquid crystal compounds.

2. Background Description

Liquid crystals are useful primarily as dielectrics in indicating devices, since the optical properties of such substances can be influenced by an electric field. Electro-optical devices based on liquid crystals are well known to the person skilled in the art and can be based on various effects such as, for example, dynamic scattering, the deformation of aligned phase (DAP type), the Schadt-Helfrich effect (rotation cell), the guest/host effect ("guest/host cell") or a cholesteric-nematic phase transition.

Since, in general, it is not possible to achieve all desired properties, such as, for example, high chemical and photochemical stability, low viscosity, large nematic or cholesteric mesophase ranges, short response times and the like, with a single compound, mixtures of several components are usually used. As a rule, such mixtures mainly contain compounds having a low viscosity, but these compounds on the other hand usually also have low clearing points. For this reason, substances which increase the clearing point must be added to the mixtures.

Liquid crystals have also previously been used as stationary phases in gas chromatography. However, the hitherto known liquid crystalline stationary phases generally have the disadvantage that they can be used only up to temperatures of about 180° C.

It has now been found that the compounds of the invention form very large mesophase ranges with high clearing points and that they generally exhibit a nematic mesophase in the entire liquid crystalline range or at least in a large part of it. They have a good chemical and photochemical stability and they are colourless. The viscosity values are comparatively low taking into consideration the high clearing points. Those compounds of formula I in which $R^2$ signifies cyano or p-cyanophenyl have a positive dielectric anisotropy; the remaining compounds of formula I (i.e. those in which $R^2$ signifies p-alkylphenyl or trans-4-alkylcyclohexyl) have small absolute values of the dielectric anisotropy.

On the basis of their very good separation capability and their high clearing points and boiling points the compounds of the invention are excellently suited for or as stationary phases in gas chromatography and can also be used at very high working temperatures. The compounds in accordance with the invention are especially suitable for the separation of isomer mixtures which can not be separated or which can be separated only with difficulty using conventional stationary phases, such as, for example, cis/trans-isomeric cyclopentanes and cyclohexanes (e.g. 1,4-disubstituted cyclohexanes), isomeric aromatic hydrocarbons (e.g. o-, m- and p-disubstituted benzenes, anthracene/phenanthrene), double bond isomers (e.g. unsaturated fatty acid esters) and the like. The compounds in accordance with the invention are also especially suitable for use in capillary columns. Further, the compounds of formula I in which X signifies the group —CH₂CH₂— are also especially suitable for the separation of silylated samples. Such samples of silyl derivatives (e.g. trimethylsilyl derivatives) are frequently prepared when mixtures of compounds having acidic hydrogen atoms (e.g. acids, alcohols, phenols, amines, amides) are present in order to facilitate the separation.

Furthermore, the compounds of the invention are suitable as clearing point-increasing substances for liquid crystalline dielectrics. In this case they primarily have the advantage that either very large clearing point increases can be achieved or on the other hand only comparatively small amounts need be added to achieve a particular clearing point increase and thus the remaining properties of the mixture are altered only insignificantly.

SUMMARY OF THE INVENTION

The present invention concerns novel liquid crystalline compounds, namely 4'-(trans-4-alkylcyclohexyl)-4-biphenylyl derivatives and 4-(trans-4-alkylcyclohexyl)-phenyl derivatives of the formula

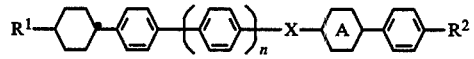

wherein n stands for the number 1 and X stands for the group —COO—, —OOC— or —CH₂CH₂—, or n stands for the number 0 and X stands for the group —CH₂CH₂—; ring A denotes p-phenylene or trans-1,4-cyclohexylene; $R^2$ represents cyano, p-cyanophenyl or, insofar as X stands for —COO— or —OOC—, also p-$R^3$-phenyl or trans-4-$R^3$-cyclohexyl; and $R^1$ and $R^3$ signify straight-chain $C_1$-$C_{10}$-alkyl.

The invention is also concerned with the manufacture of the compounds of formula I above, liquid crystalline mixtures which contain compounds of formula I above as well as their use for electro-optical and chromatographic purposes.

DETAILED DESCRIPTION OF THE INVENTION

Figure 1:
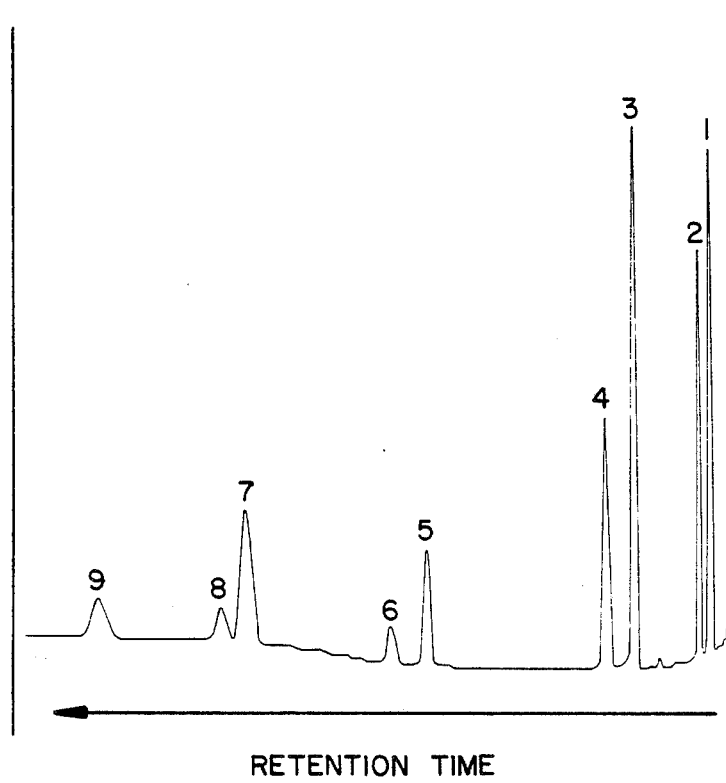
FIG. 1 represents a chromatogram showing the separation of aromatic hydrocarbons which is described in Example 9.

The present invention concerns a liquid crystalline compound of the formula:

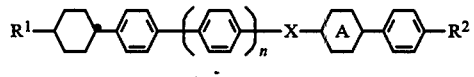

wherein
n is 1 and X is —COO—, —OOC— or —CH₂CH₂—; or
n is 0 and X is —CH₂CH₂—;
ring A is p-phenylene or trans-1,4-cyclohexylene;
$R^2$ is cyano, p-cyanophenyl or, when X is —COO— or —OOC—, $R^2$ may also be p-$R^3$-phenyl or trans-4-$R^3$-cyclohexyl; and
$R^1$ and $R^3$ each are straight-chain $C_1$-$C_{10}$-alkyl.

The invention is also concerned with the manufacture of the compounds of formula I above, liquid crystalline mixtures which contain compounds of formula I above as well as their use for electro-optical and chromatographic purposes.

It has now been found that the inventive compounds form very large mesophase ranges with high clearing points and that they generally exhibit a nematic mesophase in the entire liquid crystalline range or at least in a large part of it. They have a good chemical and photochemical stability and they are colourless. The viscosity values are comparatively low taking into consideration the high clearing points. Those compounds of formula I in which $R^2$ signifies cyano or p-cyanophenyl have a positive dielectric anisotropy; the remaining compounds of formula I (i.e. those in which $R^2$ signifies p-alkylphenyl or trans-4-alkylcyclohexyl) have small absolute values of the dielectric anisotropy.

On the basis of their very good separation capability and their high clearing points and boiling points the compounds of the invention are excellently suited for or as stationary phases in gas chromatography and can also be used at very high working temperatures. The compounds in accordance with the invention are especially suitable for the separation of isomer mixtures which can not be separated or which can be separated only with difficulty using conventional stationary phases, such as, for example, cis/trans-isomeric cyclopentanes and cyclohexanes (e.g. 1,4-disubstituted cyclohexanes), isomeric aromatic hydrocarbons (e.g. o-, m- and p-disubstituted benzenes, anthracene/phenanthrene), double bond isomers (e.g. unsaturated fatty acid esters) and the like. The compounds in accordance with the invention are also especially suitable for use in capillary columns. Further, the compounds of formula I in which X signifies the group —CH$_2$CH$_2$— are also especially suitable for the separation of silylated samples. Such samples of silyl derivatives (e.g. trimethylsilyl derivatives) are frequently prepared when mixtures of compounds having acidic hydrogen atoms (e.g. acids, alcohols, phenols, amines, amides) are present in order to facilitate the separation.

Furthermore, the compounds of the invention are suitable as clearing point-increasing substances for liquid crystalline dielectrics. In this case they primarily have the advantage that either very large clearing point increases can be achieved or, on the other hand, only comparatively small amounts need be added to achieve a particular clearing point increase and thus the remaining properties of the mixture are altered only insignificantly.

Unless otherwise stated, "$C_1$-$C_{10}$ alkyl" as used throughout this application denotes a straight-chain alkyl group of 1 to 10 carbon atoms. Exemplary straight-chain alkyl groups are methyl, ethyl, propyl, butyl, pentyl, hexyl, heptyl, octyl, nonyl and decyl.

Unless otherwise stated, the term "halogen" or "halide" denotes fluorine, chlorine, bromine, or iodine.

The compounds in accordance with the invention are tetracyclic, pentacyclic or hexacyclic compounds having 1 or 2 polar groups, namely an ester group and/or a cyano group. The alkyl groups $R^1$ and $R^3$ signify independently of each other methyl, ethyl, propyl, butyl, pentyl, hexyl, heptyl, octyl, nonyl and decyl.

The group $R^2$ in formula I above preferably denotes cyano, p-cyanophenyl or p-$R^3$-phenyl when ring A signifies trans-1,4-cyclohexylene, and $R^2$ preferably denotes trans-4-$R^3$-cyclohexyl when ring A signifies p-phenylene. X preferably stands for the group —COO— or —CH$_2$CH$_2$—. The alkyl groups $R^1$ and $R^3$ preferably signify independently of each other straight-chain $C_1$-$C_7$-alkyl and especially propyl, butyl or pentyl. Preferably, n stands for the number 1. Even more preferred are compounds wherein $R^2$ is p-$R^3$-phenyl or trans-4-$R^3$-cyclohexyl and $R^3$ is propyl, butyl or pentyl.

Examples of preferred compounds in accordance with the invention are the compounds of formula I above in which $R^1$, X, ring A and $R^2$ have the significances given in Table 1 (—C$_6$H$_4$— denotes p-phenylene and —C$_6$H$_{10}$— denotes trans-1,4-cyclohexylene) and n stands for the number 1, as well as the compounds of formula I named in the detailed examples hereinafter.

TABLE 1

| $R^1$ | X | Ring A | $R^2$ |
|---|---|---|---|
| C$_3$H$_7$— | —CH$_2$CH$_2$— | —C$_6$H$_{10}$— | —CN |
| C$_4$H$_9$— | —CH$_2$CH$_2$— | —C$_6$H$_{10}$— | —CN |
| C$_5$H$_{11}$— | —CH$_2$CH$_2$— | —C$_6$H$_{10}$— | —CN |
| C$_3$H$_7$— | —CH$_2$CH$_2$— | —C$_6$H$_{10}$— | —C$_6$H$_4$—CN |
| C$_4$H$_9$— | —CH$_2$CH$_2$— | —C$_6$H$_{10}$— | —C$_6$H$_4$—CN |
| C$_5$H$_{11}$— | —CH$_2$CH$_2$— | —C$_6$H$_{10}$— | —C$_6$H$_4$—CN |
| C$_3$H$_7$— | —COO— | —C$_6$H$_{10}$— | —CN |
| C$_4$H$_9$— | —COO— | —C$_6$H$_{10}$— | —CN |
| C$_5$H$_{11}$— | —COO— | —C$_6$H$_{10}$— | —CN |
| C$_3$H$_7$— | —COO— | —C$_6$H$_{10}$— | —C$_6$H$_4$—CN |
| C$_4$H$_9$— | —COO— | —C$_6$H$_{10}$— | —C$_6$H$_4$—CN |
| C$_5$H$_{11}$— | —COO— | —C$_6$H$_{10}$— | —C$_6$H$_4$—CN |
| C$_3$H$_7$— | —COO— | —C$_6$H$_4$— | —CN |
| C$_5$H$_{11}$— | —COO— | —C$_6$H$_4$— | —CN |
| C$_3$H$_7$— | —COO— | —C$_6$H$_4$— | —C$_6$H$_4$—CN |
| C$_5$H$_{11}$— | —COO— | —C$_6$H$_4$— | —C$_6$H$_4$—CN |
| C$_3$H$_7$— | —COO— | —C$_6$H$_4$— | —C$_6$H$_{10}$—C$_3$H$_7$ |
| C$_4$H$_9$— | —COO— | —C$_6$H$_4$— | —C$_6$H$_{10}$—C$_3$H$_7$ |
| C$_5$H$_{11}$— | —COO— | —C$_6$H$_4$— | —C$_6$H$_{10}$—C$_3$H$_7$ |
| C$_3$H$_7$— | —COO— | —C$_6$H$_4$— | —C$_6$H$_{10}$—C$_4$H$_9$ |
| C$_4$H$_9$— | —COO— | —C$_6$H$_4$— | —C$_6$H$_{10}$—C$_4$H$_9$ |
| C$_5$H$_{11}$— | —COO— | —C$_6$H$_4$— | —C$_6$H$_{10}$—C$_4$H$_9$ |
| C$_3$H$_7$— | —COO— | —C$_6$H$_4$— | —C$_6$H$_{10}$—C$_5$H$_{11}$ |
| C$_4$H$_9$— | —COO— | —C$_6$H$_4$— | —C$_6$H$_{10}$—C$_5$H$_{11}$ |
| C$_5$H$_{11}$— | —COO— | —C$_6$H$_4$— | —C$_6$H$_{10}$—C$_5$H$_{11}$ |
| C$_3$H$_7$— | —COO— | —C$_6$H$_{10}$— | —C$_6$H$_4$—C$_3$H$_7$ |
| C$_5$H$_{11}$— | —COO— | —C$_6$H$_{10}$— | —C$_6$H$_4$—C$_3$H$_7$ |
| C$_3$H$_7$— | —COO— | —C$_6$H$_{10}$— | —C$_6$H$_4$—C$_5$H$_{11}$ |
| C$_5$H$_{11}$— | —COO— | —C$_6$H$_{10}$— | —C$_6$H$_4$—C$_5$H$_{11}$ |
| C$_3$H$_7$— | —COO— | —C$_6$H$_4$— | —C$_6$H$_4$—C$_5$H$_{11}$ |
| C$_3$H$_7$— | —COO— | —C$_6$H$_{10}$— | —C$_6$H$_{10}$—C$_5$H$_{11}$ |
| C$_3$H$_7$— | —OOC— | —C$_6$H$_{10}$— | —CN |
| C$_5$H$_{11}$— | —OOC— | —C$_6$H$_{10}$— | —CN |
| C$_3$H$_7$— | —OOC— | —C$_6$H$_{10}$— | —C$_6$H$_4$—CN |
| C$_5$H$_{11}$— | —OOC— | —C$_6$H$_{10}$— | —C$_6$H$_4$—CN |
| C$_3$H$_7$— | —OOC— | —C$_6$H$_{10}$— | —C$_6$H$_4$—C$_3$H$_7$ |
| C$_4$H$_9$— | —OOC— | —C$_6$H$_{10}$— | —C$_6$H$_4$—C$_3$H$_7$ |
| C$_5$H$_{11}$— | —OOC— | —C$_6$H$_{10}$— | —C$_6$H$_4$—C$_3$H$_7$ |
| C$_3$H$_7$— | —OOC— | —C$_6$H$_{10}$— | —C$_6$H$_4$—C$_5$H$_{11}$ |
| C$_5$H$_{11}$— | —OOC— | —C$_6$H$_{10}$— | —C$_6$H$_4$—C$_5$H$_{11}$ |
| C$_3$H$_7$— | —OOC— | —C$_6$H$_{10}$— | —C$_6$H$_{10}$—C$_5$H$_{11}$ |
| C$_5$H$_{11}$— | —OOC— | —C$_6$H$_{10}$— | —C$_6$H$_{10}$—C$_3$H$_7$ |

The compounds of formula I can be manufactured in accordance with the invention by the following methods:

(a) the compounds of formula I in which X signifies the group —COO— or —OOC—, can be manufactured by esterifying a compound of the formula:

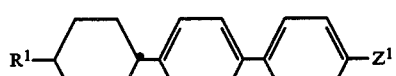

II and a compound of the formula:

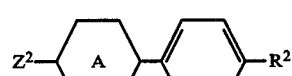

III wherein one of the groups $Z^1$ and $Z^2$ denotes the carboxyl group and the other denotes the hydroxy group and $R^1$, $R^2$ and ring A have the significances given in formula I.
or reactive derivatives of these compounds;

(b) the compounds of formula I in which X signifies the group —CH₂CH₂—, can be manufactured by catalytically hydrogenating a compound of the formula:

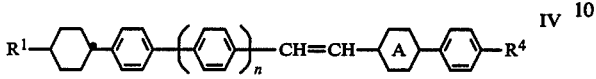         IV wherein $R^4$ represents cyano or p-cyanophenyl and $R^1$, n and ring A have the significances given in formula I.

The esterification of the compounds of formulae II and III can be carried out in a manner known per se by esterification of the carboxylic acid or a reactive derivative thereof (e.g. acid chloride, bromide or anhydride) with the hydroxy compound or a suitable salt thereof (e.g. the sodium salt). A preferred method comprises reacting the acid chloride (which is obtainable from the carboxylic acid e.g. by heating with thionyl chloride) with the hydroxy compound. This reaction is conveniently carried out in an inert organic solvent, for example an ether (such as diethyl ether or tetrahydrofuran) or dimethylformamide, benzene, toluene, cyclohexane, carbon tetrachloride and the like. The hydrogen chloride which is liberated can be taken up with an acid-binding agent (e.g. a tertiary amine or pyridine). The acid-binding agent can also simultaneously serve as the solvent. Other preferred methods comprise reacting the carboxylic acid with the hydroxy compound in the presence of 4-(dimethylamino)pyridine and dicyclohexylcarbodiimide or in the presence of oxalyl chloride and dimethylformamide. The temperature and pressure at which the above esterification is carried out are not critical. However, the esterification is generally carried out at atmospheric pressure and at a temperature between about −30° C. and the boiling temperature of the reaction mixture.

The catalytic hydrogenation of the compounds of formula IV can be carried out in a manner known per se and with customary hydrogenation catalysts, for example with palladium, platinum, Raney-nickel and the like, preferably with palladium. As solvents there can be used any inert organic solvents such as saturated alcohols, ethers, esters, carboxylic acids, hydrocarbons and the like, for example ethanol, dioxan, tetrahydrofuran, ethyl acetate, glacial acetic acid, toluene or hexane. The temperature and pressure are not critical. However, the catalytic hydrogenation is generally carried out at a temperature between room temperature and the boiling temperature of the reaction mixture and at a pressure of about 1 to about 5 atmospheres.

The compounds of formula IV are novel and are also an object of the present invention. The trans-isomers of the compounds of formula IV (i.e. the compounds having a trans double bond) are liquid crystalline compounds with very large mesophase ranges.

The compounds of formula IV can be obtained according to methods known per se for the Wittig reaction from a [(4'-(trans-4-alkylcyclohexyl)-4-biphenylyl)-methyl]triphenylphosphonium bromide or a [p-(trans-4-alkylcyclohexyl)benzyl]triphenylphosphonium bromide and an aldehyde of the formula:

         V wherein ring A denotes p-phenylene or trans-1,4-cyclohexylene and $R^4$ represents cyano or p-cyanophenyl.

The aldehydes of formula V are novel and are also an object of the invention.

The compounds of formula V in which ring A denotes p-phenylene can be obtained, for example, by converting biphenyl-4,4'-dicarboxylic acid or p-terphenyl-4,4''-dicarboxylic acid into the monoester (e.g. with diazomethane), converting the monoester with thionyl chloride, ammonia and phosphorus oxychloride via the acid chloride and amide into the cyanoester, saponifying the cyanoester with sodium hydroxide and converting the cyanoacid into the cyanoaldehyde by reaction with thionyl chloride and Rosenmund reduction.

The compounds of formula V in which ring A denotes trans-1,4-cyclohexylene can be obtained, for example, by a Wittig reaction of 4-(p-cyanophenyl)cyclohexanone or 4-(4'-cyano-4-biphenylyl)cyclohexanone with triphenyl-methoxymethylphosphonium chloride and subsequent hydrolysis of the enol ether.

The compounds of formula III in which $Z^2$ denotes the carboxyl group and $R^2$ signifies cyano or p-cyanophenyl can be obtained, for example, from the compounds of formula V by Jones' oxidation or by oxidation with pyridinium dichromate. The compounds of formula III in which $Z^2$ denotes the hydroxy group and $R^2$ signifies cyano or p-cyanophenyl can be obtained, for example, by reducing 4-(p-cyanophenyl)cyclohexanone or 4-(4'-cyano-4-biphenylyl)cyclohexanone with sodium borohydride. The remaining compounds of formulae II and III are known or are analogues of known compounds and can be obtained according to known methods.

The use of the compounds in accordance with the invention for or as liquid crystalline stationary phases in gas chromatography can be carried out in a manner known per se and on usual carrier materials. The compounds in accordance with the invention can be used in pure form or also as mixtures of two or more compounds of formula I with one another or as mixtures of one or more compounds of formula I with one or more additional suitable substances.

The invention is therefore also concerned with liquid crystalline mixtures having at least two components, wherein at least one component is a compound of formula I above.

In order to avoid a gradual change of the composition when used over a long period, for chromatographic applications there are preferably admixed only compounds having comparable low evaporation pressures. The amount of compounds of formula I in the liquid crystalline mixtures for chromatographic purposes can vary in wide limits and can amount to about 1–100 wt.%. However, the amount of compounds of formula I generally amounts to at least about 50 wt.%.

The compounds in accordance with the invention are also suitable for electro-optical applications and can be used in the form of mixtures with other substances which are suitable for liquid crystalline dielectrics, such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, terphenyls, phenylcyclohexanes, cyclohexylbiphenyls, phenylpyrimidines, phenyldioxanes, 2-cyclohexyl-1-phenylethanes, pyridazines, 2,3-dicyano-1,4-phenylene derivatives and the like. Such substances are known to the person skilled in the art and many of them are, moreover, commercially available. The amount of compounds of formula I in liquid crystalline mixtures for electro-optical applications preferably amounts to about 1–30 wt.% and particularly to about 2–15 wt.%.

Because of the strong clearing point-increasing action of the compounds in accordance with the invention they are primarily suitable for liquid crystalline dielectrics which contain substances having relatively small mesophase ranges or even monotropic or non-liquid crystalline substances. There are especially preferred those mixtures which contain one or more compounds of formula I and one or more of the compounds of the following formulae:

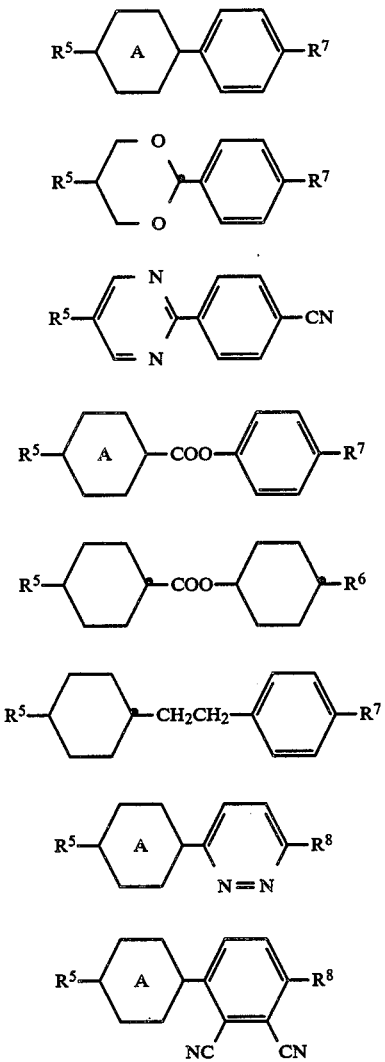

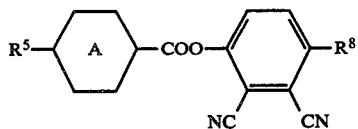

wherein ring A stands for p-phenylene or trans-1,4-cyclohexylene, $R^5$ and $R^6$ represent straight-chain $C_1$–$C_7$-alkyl, $R^7$ denotes cyano, straight-chain $C_1$–$C_7$-alkyl or straight-chain $C_1$–$C_7$-alkoxy and $R^8$ signifies straight-chain $C_1$–$C_7$-alkyl or straight-chain $C_1$–$C_7$-alkoxy.

The dielectrics in accordance with the invention can also contain suitable optically active compounds (e.g. optically active biphenyls) and/or dichroic colouring substances (e.g. azo, azoxy or anthraquinone colouring substances). The amount of such compounds is determined by the solubility and the desired pitch, colour, extinction and the like. Preferably, the amount of optically active compounds is at most about 4 wt.% and the amount of dichroic colouring substances is at most about 10 wt.%.

The manufacture of the liquid crystalline mixtures and of the electro-optical devices can be carried out in a manner known per se.

The following Examples illustrate the manufacture of the compounds provided by the invention, the preparation of certain starting materials as well as the use of the inventive compounds in chromatography. Unless otherwise stated, percentages and ratios relating to solvent mixtures are expressed in volume, purity data determined by gas chromatography are expressed in area %, and the remaining percentages and ratios are expressed in weight. Temperatures are in degress Celsius (°C.), normal pressure is about 1 atmosphere, and room temperature is about 23° C. In the Examples C denotes a crystalline phase, S denotes a smectic phase, N denotes a nematic phase, and I denotes the isotropic phase. Unless indicated otherwise, the Examples were carried out as written.

EXAMPLE 1

2.029 g of p-[trans-4-[2-(4'-(trans-4-pentylcyclohexyl)-4-biphenylyl)vinyl]cyclohexyl]benzonitrile were dissolved in 150 ml of toluene/ethanol (vol. 4:1), treated with 0.3 g of palladium/carbon (10%) and hydrogenated at room temperature until the hydrogen uptake came to a standstill. The reaction mixture was subsequently suction filtered, the residue was rinsed with dichloromethane and the filtrate was evaporated. The colourless, solid crude product obtained was then dissolved in toluene and chromatographed on silica gel with toluene, thus isolating 1.255 g of substance which was recrystallized from dichloromethane/hexane and dried in a high vacuum at 20° C. over phosphorus pentoxide. Yield: 0.894 g of pure p-[trans-4-[2-(4'-(trans-4-pentylcyclohexyl)-4-biphenylyl)ethyl]cyclohexyl]benzonitrile: (C-C) 134.5°–135° C., m.p. (C-S, 147°–147.5° C., (S-N) 167.5°–169° C., cl.p. (N-I) 370° C.

The p-[trans-4-[2-(4'-(trans-4-pentylcyclohexyl)-4-biphenylyl)vinyl]cyclohexyl]benzonitrile used as the starting material was prepared as follows:

(a) A suspension of 10.4 g of triphenyl-methoxymethyl-phosphonium chloride in 60 ml of t-butyl methyl ether was placed at −10° C. under argon gasification and treated within 10 minutes with 3.6 g of solid potassium t-butylate. After completion of the addition the reaction mixture was stirred at −10° C. to 0° C. for another 30 minutes and then treated dropwise at 0° C. with a solution of 4.2 g of 4-(p-cyanophenyl)cyclohexanone in 50 ml of absolute tetrahydrofuran. The reaction mixture was subsequently stirred at room temperature for another 2 hours, then poured into 500 ml of hexane and filtered. Low-pressure chromatography (0.5 bar) of the concentrated residue (7.1 g) on silica gel with ethyl acetate/petroleum ether (vol. 1:19) gave 4.5 g (94%) of p-[4-(methoxymethylene)cyclohexyl]benzonitrile as a colourless, gradually crystallizing oil (purity 95%); Rf-value (ethyl acetate/petroleum ether vol. 1:9)=0.30.

(b) A mixture of 14.25 g of p-[4-(methoxymethylene)-cyclohexyl]benzonitrile (purity 96.1%) and 200 ml of tetrahydrofuran/2N hydrochloric acid (vol. 4:1) was heated to reflux for 30 minutes. The reaction mixture was subsequently poured into 300 ml of water and extracted three times with 200 ml of diethyl ether each time. The organic phases were washed with 200 ml of water, dried over magnesium sulphate and concentrated. There were thus obtained 13.75 g (103%) of crude product of 4-(p-cyanophenyl)cyclohexanecarboxaldehyde (trans/cis ratio about 3:1) as a colourless, slowly crystallizing oil. Recrystallization of this material from 1.3 l of hexane gave 3.71 g (29%) of trans-4-(p-cyanophenyl)cyclohexanecarboxaldehyde (purity 99.5%) as long, colourless needles of m.p. 57.1° C. The mother liquor was concentrated to a volume of 1 l and again set aside for crystallization, there being obtained as the second crystallizate 1.20 g of colourless needles containing 97% of trans-aldehyde and 3% of cis-aldehyde. The separated mother liquor was now concentrated, the residue was again heated to reflux for 30 minutes in 100 ml of tetrahydrofuran/2N hydrochloric acid (vol. 4:1) and the mixture was then worked-up in the same manner as on the first occasion. The crude product obtained was combined with the second crystallizate (1.2 g) and recrystallized from 900 ml of hexane, whereby 3.56 g (28%) of trans-4-(p-cyanophenyl)-cyclohexanecarboxaldehyde (purity 99.7%) could again be isolated as long, colourless needles. The mother liquor (containing 4.2 g of crude product) was no longer worked-up. Total yield after two cycles: 7.27 g (57%) of trans-4-(p-cyanophenyl)cyclohexanecarboxaldehyde; m.p. 57.1° C.

(c) 4.652 g of [(4'-(trans-4-pentylcyclohexyl)-4-biphenylyl)methyl]-triphenylphosphonium bromide were suspended in 40 ml of absolute t-butyl methyl ether while stirring and under nitrogen gasification, the mixture was then treated with 0.789 g of potassium t-butylate and stirred at room temperature for a further 1 hour. The orange suspension was subsequently cooled to −60° C. and treated dropwise within 15 minutes with a solution of 1.0 g of trans-4-(p-cyanophenyl)cyclohexanecarboxaldehyde in 8 ml of absolute t-butyl methyl ether. 5 ml of absolute t-butyl methyl ether were rinsed through the dropping funnel and the temperature of the reaction mixture was then left to rise to −25° C. within 1.25 hours. The reaction mixture was subsequently poured into 75 ml of water and extracted three times with toluene. The organic extracts were washed once with water, dried over sodium sulphate and evaporated in vacuo. The residual, solid, colourless product (5.0 g) was suspended in hexane and chromatographed on silica gel. Elution with hexane and hexane/toluene (vol. 9:1) yielded 0.653 g of colourless 4-methyl-4'-(trans-4-pentylcyclohexyl)biphenyl [m.p. (C-N) 98.9° C., cl.p. (N-I) 175.3° C.] and elution with hexane/toluene (vol. 1:1), toluene and toluene/acetone (containing 1–10 vol.% of acetone) finally yielded 2.029 g of p-[trans-4-[2-(4'-(trans-4-pentylcyclohexyl)-4-biphenylyl)vinyl]-cyclohexyl]benzonitrile as a colourless to yellowish reaction product which was used for the subsequent hydrogenation without further purification.

The following compounds were manufactured in an analogous manner:

p-[trans-4-[2-(4-(trans-4-pentylcyclohexyl)phenyl)ethyl]cyclohexyl]benzonitrile; m.p. (C-N) 99.6° C., (S-N) 76.5° C., cl.p. (N-I) 265.0° C., p-[trans-4-[2-(4'-(trans-4-butylcyclohexyl)-4-biphenylyl)ethyl]cyclohexyl]benzonitrile; m.p. (C-N) 174.6° C., cl.p. (N-I) 378.5° C.

EXAMPLE 2

A mixture of 1.0 g of trans-4-(p-cyanophenyl)cyclohexanol, 1.75 g of 4'-(trans-4-pentylcyclohexyl)-4-biphenylcarboxylic acid, 1.2 g of dicyclohexylcarbodiimide and 98 mg of 4-(dimethylamino)pyridine in 60 ml of dichloromethane was stirred at room temperature for 18 hours under argon gasification. The beige suspension was subsequently filtered (rinsing with dichloromethane) and the filtrate was concentrated. Low-pressure chromatography (0.5 bar) of the residue (3.1 g) on silica gel with toluene yielded 1.2 g (45%) of pure 4'-(trans-4-pentylcyclohexyl)-4-biphenylcarboxylic acid trans-4-(p-cyanophenyl)cyclohexyl ester. Recrystallization from ethyl acetate/acetone (vol. 1:4) gave white crystals of m.p. (C-N) 148.6° C. and cl.p. (N-I) 347° C.; purity 99.6%.

The trans-4-(p-cyanophenyl)cyclohexanol used as the starting material was prepared as follows:

51.0 g of 4-(p-cyanophenyl)cyclohexanone were almost completely dissolved in 1.5 l of ethanol/water (vol. 4:1) and then treated within 10 minutes with 9.68 g of sodium borohydride. The mixture was stirred for a further 30 minutes and then left to stand overnight. The reaction mixture was subsequently treated cautiously with 350 ml of dilute, ice-cold hydrochloric acid (1 part of concentrated hydrochloric acid to 4 parts of water), then treated with 2 l of water and 1 l of diethyl ether and shaken. The aqueous phase was separated and extracted four times with 0.5 l of diethyl ether each time. The combined organic phases were washed with 100 ml of saturated sodium hydrogen carbonate solution and with 100 ml of saturated sodium chloride solution, dried over sodium sulphate and concentrated. The crude product, which still contained water, was dried further by dissolution in toluene and acetone and concentration. The beige, solid residue (48.9 g) was dissolved in 300 ml of hot toluene and a fine, insoluble residue was filtered off while the mixture was hot. The filtrate was cooled to −20° C. and the crystallizate obtained was filtered off under suction, washed with 50 ml of toluene/hexane (vol. 9:1) and dried. There were thus obtained 31.72 g (61.6%) of pure, light beige trans-4-(p-cyanophenyl)cyclohexanol of m.p. 119.5°–122.4° C. A further 3.21 g (6.2%) of trans-4-(p-cyanophenyl)cyclohexanol of m.p. 116.5°–122.1° C. were obtained from the mother liquor by crystallization from 60 ml of toluene at −20° C.

The following compounds were manufactured in an analogous manner:

4'-(Trans-4-propylcyclohexyl)-4-biphenylcarboxylic acid trans-4-(p-cyanophenyl)cyclohexyl ester; m.p. (C-N) 189.6° C., cl.p. (N-I) 350° C., 4'-(trans-4-butylcyclohexyl)-4-biphenylcarboxylic acid trans-4-(p-cyanophenyl)cyclohexyl ester; m.p. (C-N) 168.6° C. or 169.8° C. (2 modifications), cl.p. (N-I) 348.5° C.

EXAMPLE 3

A solution of 2.40 g of 4-hydroxy-4'-(trans-4-pentylcyclohexyl)biphenyl and 0.149 g of 4-(dimethylamino)-pyridine in 125 ml of absolute dichloromethane was treated while stirring with 2.40 g of 4'-(trans-4-propylcyclohexyl)-4-biphenylcarboxylic acid. The yellowish suspension was diluted with 25 ml of absolute dichloromethane, treated with 1.843 g of solid dicyclohexylcarbodiimide and again with 35 ml of absolute dichloromethane (rinsing), then stirred at room temperature for 24 hours and subsequently heated to reflux for 4 hours. After cooling to room temperature the precipitate was filtered off under suction, washed with dichloromethane and dried, thereby obtaining 3.057 g of a colourless, solid product. Concentration of the filtrate to dryness in vacuo gave 3.7 g of a yellow, solid substance which was suspended in dichloromethane and evaporated in vacuo together with 15 g of silica gel. The residue was suspended in toluene and added to a column of silica gel in toluene. Elution with toluene, toluene/1% acetone and toluene/2% acetone gave 1.823 g of crude ester. After repeated recrystallization from dichloromethane/hexane and drying in a high vacuum over phosphorus pentoxide for 16 hours there was obtained 0.762 g of pure 4'-(trans-4-propylcyclohexyl)-4-biphenylcarboxylic acid 4'-(trans-4-pentylcyclohexyl)-4-biphenylyl ester; (C-C) 132° C., m.p. (C-S) 200° C., (S-S) 219° C., (S-N) 224° C., cl.p. (N-I) 462° C. The initially obtained, colourless, solid product (3.057 g) was suspended in dichloromethane together with the mother liquors obtained in the above recrystallizations and chromatographed on silica gel in dichloromethane. Elution with dichloromethane and dichloromethane/2% acetone yielded 2.467 g of yellowish, crystalline ester. Repeated recrystallization of this crude product from dichloromethane/hexane and drying in a high vacuum over phosphorus pentoxide gave a further 1.916 g of pure product and 0.502 g of slightly contaminated product.

EXAMPLE 4

(a) A suspension of 1.07 g of aluminium chloride in 10 ml of 1,2-dichloroethane was placed at room temperature under argon gasification, treated within 10 minutes with a solution of 2.0 g of 4-(4-biphenylyl)cyclohexanone in 10 ml of 1,2-dichloroethane and stirred for another 30 minutes. The resulting brown-violet suspension was added dropwise at room temperature within 10 minutes to a mixture of 1.07 g of aluminium chloride in 10 ml of 1,2-dichloroethane which had previously been treated at room temperature with 1.37 ml of oxalyl chloride. The reaction mixture was stirred at room temperature for a further 30 minutes and then treated cautiously (strong exothermic reaction) with 30 ml of a 30% (wt./vol.) potassium chloride solution while cooling to about 0° C. within 25 minutes. The resulting, beige suspension was poured on to 200 ml of ice-water and extracted three times with 200 ml of methylene chloride each time. The organic phases were washed twice with 100 ml of ice-water each time, dried over magnesium sulphate and concentrated to a volume of about 35 ml. This solution was added within 10 minutes to a mixture of 4.5 ml of 25% (wt./vol.) aqueous ammonia solution and 3 ml of water placed at about 15° C. in a sulphonation flask with a dropping funnel and a mechanical stirrer. The heterogeneous reaction mixture was stirred at room temperature for a further 1.75 hours. The resulting, beige precipitate was then filtered off and washed well with water. After drying in a high vacuum there were obtained 1.66 g (71%) of 4'-(4-oxocyclohexyl)-4-biphenylcarboxamide as a beige, amorphous powder; Rf-value (chloroform/methanol vol. 19:1)=0.36.

(b) A mixture of 1.50 g of 4'-(4-oxocyclohexyl)-4-biphenylcarboxamide and 20 ml of pyridine was placed at 0° C. under argon gasification and treated with 463 Ml of mesyl chloride. The cooling bath was removed and the yellow suspension was stirred at room temperature for 19 hours. Subsequently, a further 1.4 ml of mesyl chloride were added to the reaction mixture at room temperature and the mixture was stirred at 60° C. for 67 hours, the cooled, dark brown reaction mixture was made acid with 40 ml of ice-cold, 25% (wt./vol.) hydrochloric acid and extracted three times with 100 ml of methylene chloride each time. The organic phases were washed three times with 50 ml of water each time, dried over magnesium sulphate and concentrated. Low-pressure chromatography (0.5 bar) of the red-brown crystalline residue (0.9 g) on silica gel with chloroform gave in the main run after additional treatment with active carbon in chloroform at 60° C. 300 mg (21%) of 4-(4'-cyano-4-biphenylyl)cyclohexanone as light yellow crystals; Rf-value (chloroform)=0.43.

(c) 4-(4'-Cyano-4-biphenylyl)cyclohexanone can be converted in an analogous manner to Example 1 into trans-4-(4'-cyano-4-biphenylyl)-cyclohexanecarboxaldehyde and 4'-[trans-4-[2-(4'-(trans-4-alkylcyclohexyl)-4-biphenylyl)ethyl]cyclohexyl]-4-biphenylcarbonitrile. Further, in an analogous manner to Example 2 4-(4'-cyano-4-biphenylyl)cyclohexanone can be converted into trans-4-(4'-cyanobiphenylyl)cyclohexanol and 4-(trans-4-alkylcyclohexyl)-4-biphenylcarboxylic acid trans-4-(4'-cyano-biphenylyl)cyclohexyl ester.

EXAMPLE 5

A solution of 0.214 g of 4'-[trans-4-[2-(4'-(trans-4-pentylcyclohexyl)-4-biphenylyl)vinyl]cyclohexyl]-4-biphenylcarbonitrile in 200 ml of tetrahydrofuran was treated with 52.5 mg of palladium/carbon (5%) and hydrogenated at room temperature until the hydrogen uptake came to a stand-still (1.75 hours). The reaction mixture was subsequently gassed with nitrogen and suction filtered (rinsing with hot tetrahydrofuran). After concentrating the filtrate in vacuo and drying at 50° C. under a water-jet vacuum there was obtained 0.310 g of colourless, solid 4'-[trans-4-[2-(4'-(trans-4-pentylcyclohexyl)-4-biphenylyl)ethyl]cyclohexyl]-4-biphenylcarbonitrile which still contained solvent. Recrystallization from tetrahydrofuran gave colourless needles with (S-N) 194.5° C. and cl.p. (N-I) 440° C.

The 4'-[trans-4-[2-(4'-(trans-4-pentylcyclohexyl)-4-biphenyl)vinyl]cyclohexyl]-4-biphenylcarbonitrile used as the starting material was prepared as follows:

A suspension of 2.337 g of [(4'-(trans-4-pentylcyclohexyl)-4-biphenylyl)methyl]triphenylphosphonium bromide in 35 ml of dry tetrahydrofuran was treated while stirring in a sulphonation flask with nitrogen gasification with 0.394 g of potassium t-butylate (rinsing with 20 ml of absolute tetrahydrofuran) and the mixture was stirred at room temperature for a further 1 hour. After cooling to −60° C. the mixture was treated dropwise within 25 minutes with a solution of 0.928 g of trans-4-(4'-cyano-4-biphenylyl)cyclohexanecarboxaldehyde [prepared from 4-(4'-cyano-4-biphenylyl)cyclohexanone in an analogous manner to Example 1(a) and (b)] in 50 ml of absolute tetrahydrofuran (rinsing with 10 ml of absolute tetrahydrofuran), the suspension was then left to warm to 7° C. within 3 hours and was finally stirred at room temperature overnight. The suspension was thereafter poured into 100 ml of water. The precipitate was filtered off under suction, washed well with water and dried, there being obtained 1.805 g of a solid, almost colourless product. From the filtrate there separated a fine precipitate which, after dilution with water to 500 ml, was almost filtered off under suction, washed with water and dried (0.222 g of a yellowish, solid substance). The two precipitates (2.027 g) were triturated with 75 ml of diethyl ether at room temperature for 10 minutes and subsequently filtered off under suction, washed with diethyl ether and dried. The resulting colourless solid (1.074 g) was suspended in 75 ml of methylene chloride and then the precipitate was filtered off under suction, washed with methylene chloride and dried. There was thus obtained 0.871 g of crude 4'-[trans-4-[2-(4'-(trans-4-pentylcyclohexyl)-4-biphenylyl)vinyl]cyclohexyl]-4-biphenylcarbonitrile as a colourless solid (Rf-value=0.46 in toluene) which was reacted further without additional purification.

EXAMPLE 6

An isomer mixture of p-[5-(cis/trans-4-pentylcyclohexyl)-2-pyrimidinyl]benzonitrile was separated on a 2 m long, packed column (internal diameter 2.2 mm), which was filled with 2 wt.% of 4'-(trans-4-propylcyclohexyl)-4-biphenylcarboxylic acid 4'-(trans-4-pentylcyclohexyl)-4-biphenylyl ester on Gaschrom Q* (applied Science Labs), 120/140 mesh, at an analysis temperature of 290° C. Nitrogen (30 ml/min.) was used as the carrier gas. The retention time was 4.3 minutes for the cis-isomer and 16 minutes for the trans-isomer. The relative retention A for the trans-isomer was therefore 3.7 (A=1.0 for the cis-isomer).

EXAMPLE 7

A mixture of methyl oleate [(Z)-isomer] and methyl elaidate [(E)-isomer] was separated on a 2 m long, packed column (internal diameter 2.2 mm), which was filled with 2 wt.% of 4'-(trans-4-pentylcyclohexyl)-4-biphenylcarboxylic acid trans-4-(p-cyanophenyl)cyclohexyl ester on Gaschrom Q* (Applied Science Labs), 120/140 mesh, at an analysis temperature of 150° C. Nitrogen (30 ml/min.) was used as the carrier gas. The retention time was 18.5 minutes for the methyl oleate and 20.8 minutes for the methyl elaidate. The relative retention A for methyl elaidate was therefore 1.13 (A=1.0 for methyl oleate).

EXAMPLE 8

A mixture of A-naphthol and β-naphthol was separated on a 2 m long, packed column (internal diameter 2.2 mm), which was filled with 2 wt.% of p-[trans-4-[2-(4'-(trans-4-pentylcyclohexyl)-4-biphenyl)ethyl]cyclohexyl]benzonitrile on Gaschrom Q* (Applied Science Labs), 120/140 mesh, at an analysis temperature of 180° C. Nitrogen (30 ml/min.) was used as the carrier gas. The retention time was 5.2 minutes for A-naphthol and 6.6 minutes for β-naphthol. The relative retention A for β-naphthol was therefore 1.2 (A=1.0 for A-naphthol).

EXAMPLE 9

A mixture of phenanthrene (1), anthracene (2), fluoranthene (3), pyrene (4), benz(a)anthracene (5), chrysene (6), benz(b)fluoranthene (7), benz(k)fluoranthene (8) and benz(a)pyrene (9) was separated on a 2 m long, packed column (internal diameter 2.2 mm), which was filled with 2 wt.% of 4'-[trans-4-[2-(4'-(trans-4-pentylcyclohexyl)-4-biphenylyl)ethyl]cyclohexyl]-4-biphenylcarbonitrile on Gaschrom Q* (Applied Science Labs), 120/140 mesh, at an analysis temperature of 230°-300° C. and a heating rate of 4° C./minute. Nitrogen (35 ml/min.) was used as the carrier gas. The chromatogram is reproduced in FIG. 1. The retention time for benz(a)pyrene was 28 minutes.

EXAMPLE 10

A mixture containing methyl oleate [(Z)-isomer] and methyl elaidate [(E)-isomer] was separated on a 2 m long, packed column (internal diameter 2.2 mm), which was filled with 2 wt.% of p-[trans-4-[2-(4-(trans-4-pentylcyclohexyl)phenyl)ethyl]cyclohexyl]benzonitrile on Gaschrom Q* (Applied Science Labs), 120/140 mesh, at an analysis temperature of 170° C. (In addition to the two isomeric esters the mixture also contained methyl stearate). Nitrogen (35 ml/min.) was used as the carrier gas. The retention time was 13.5 minutes for methyl oleate and 15 minutes for methyl elaidate. The relative retention A for methyl elaidate was therefore 1.11 (A=1.0 for methyl oleate).

EXAMPLE 11

An isomer mixture of 1-(p-tolyl)-cis/trans-4-propylcyclohexane was separated on a 2 m long, packed column (internal diameter 2.2 mm), which was filled with 2 wt.% of p-[trans-4-[2-(4-trans-4-pentylcyclohexyl)-phenyl]ethyl]cyclohexyl]benzonitrile on Gaschrom Q* (Applied Science Labs), 120/140 mesh, at an analysis temperature of 160° C. Nitrogen (35 ml/min.) was used as the carrier gas. The retention time was 6 minutes for the cis-isomer and 13.5 minutes for the trans-isomer. The relative retention A for 1-(p-tolyl)-trans-4-propylcyclohexane was therefore 2.4 [A=1.0 for 1-(p-tolyl)-cis-4-propylcyclohexane].

We claim:

1. A compound of the formula:

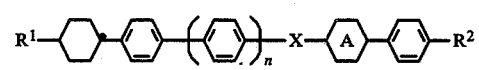

wherein
n is 1 and X is —COO—, —OOC— or —CH$_2$CH$_2$—; or
n is 0 and X is —CH$_2$CH$_2$—;
ring A is p-phenylene or trans-1,4-cyclohexylene;
$R^2$ is cyano, p-cyanophenyl or, when X is —COO— or —OOC—, $R^2$ may also be p-$R^3$-phenyl or trans-4-$R^3$-cyclohexyl;
and $R^1$ and $R^3$ each are straight-chain $C_1$-$C_{10}$-alkyl.

2. The compound of claim 1, wherein n is 1.

3. The compound of claim 1, wherein ring A is trans-1,4-cyclohexylene and $R^2$ is cyano, p-cyanophenyl or p-$R^3$-phenyl.

4. The compound of claim 1 wherein ring A is p-phenylene and $R^2$ is trans-4-$R^3$-cyclohexyl.

5. The compound of claim 1 wherein X is —COO—.

6. The compound of claim 1 wherein X is —CH$_2$CH$_2$—.

7. The compound of claim 1 wherein R$^2$ is p-R$^3$-phenyl or trans-4-R$^3$-cyclohexyl and R$^3$ is propyl, butyl or pentyl.

8. A liquid crystalline mixture having at least two components, wherein at least one component is a compound of formula I:

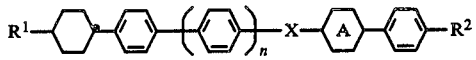

wherein
n is 1 and X is —COO—, —OOC— or —CH$_2$CH$_2$—; or n is 0 and X is —CH$_2$CH$_2$—;
ring A is p-phenylene or trans-1,4-cyclohexylene;
R$^2$ is cyano, p-cyanophenyl or, when X is —COO— or —OOC—, R$^2$ may also be p-R$^3$-phenyl or trans-4-R$^3$-cyclohexyl;
and R$^1$ and R$^3$ each are straight-chain C$_1$–C$_{10}$-alkyl.

9. An electro-optical cell comprising:
(a) two plate means;
(b) a liquid crystal means disposed between two plate means and including a compound of the formula:

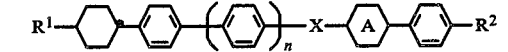

wherein
n is 1 and X is —COO—, —OOC— or —CH$_2$CH$_2$—; or n is 0 and X is —CH$_2$CH$_2$—;
ring A is p-phenylene or trans-1,4-cyclohexylene;
R$^2$ is cyano, p-cyanophenyl or, when X is —COO— or —OOC—, R$^2$ may also be p-R$^3$-phenyl or trans-4-R$^3$-cyclohexyl;
and R$^1$ and R$^3$ each are straight-chain C$_1$–C$_{10}$-alkyl; and
(c) means for applying an electrical potential to said plate means.

* * * * *